US00PP35790P2

(12) United States Plant Patent
Olesen

(10) Patent No.: US PP35,790 P2
(45) Date of Patent: May 7, 2024

(54) MINIATURE ROSE PLANT NAMED 'POULTY040'

(50) Latin Name: *Rosa hybrida*
Varietal Denomination: Poulty040

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 18/445,487

(22) Filed: Sep. 8, 2023

(30) Foreign Application Priority Data

Sep. 30, 2022 (QZ) ..... PBR 2022/2178

(51) Int. Cl.
*A01H 5/02* (2018.01)
*A01H 6/74* (2018.01)

(52) U.S. Cl.
USPC ..... Plt./122
CPC ..... *A01H 6/749* (2018.05)

(58) Field of Classification Search
USPC ..... Plt./122, 129
CPC ..... A01H 5/0222
See application file for complete search history.

(56) References Cited

PUBLICATIONS

CPVO Application Consultation Version 4.12.12 Citation for 'Poulty040'; Nov. 16, 2023; 2 pages.*

* cited by examiner

*Primary Examiner* — Kent L Bell

(57) ABSTRACT

A new rose plant of the Miniature class which has abundant, dark red flowers and attractive foliage. This new and distinct variety has shown to be uniform and stable in the resulting generations from asexual propagation.

1 Drawing Sheet

Botanical designation: *Rosa hybrida.*

Variety denomination: 'Poulty040'.

This application claims priority to Plant Breeder's Rights Application Number 2022/2178, which was filed at the Community Plant Variety Rights Office in the European Union on Sep. 30, 2022, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2017 and the resulting seeds were planted in a controlled environment in Fredensborg, Denmark. The new variety, named 'Poulty040', originated as a single seedling from the stated cross.

The new variety may be distinguished from its male pollen parent and female seed parent primarily by the following characteristics. The male pollen parent plant has red flowers with 45 petals while the new variety has dark red flowers with about 65 petals. The female seed parent plant has flowers with a general tonality of Red Group 45B while the new variety has flowers which are darker red, with a general tonality of Red Group 53B to 53C.

The objective of the hybridization of this rose variety was to create a new and distinct variety with unique qualities, such as:

1. Uniform and abundant dark red flowers;
2. Vigorous, but very compact growth when propagated on its own roots;
3. Exceptional disease resistance.

This combination of qualities is not present in previously available commercial cultivars of this type, known to the inventor, and distinguish 'Poulty040' from all other varieties of which we are aware.

As part of the rose development program, Mogens N. Olesen germinated the seeds from the aforementioned hybridization during winter of 2017 and conducted evaluations on the resulting seedlings in a controlled environment in Fredensborg, Denmark. 'Poulty040' was selected in the spring of 2018 by the inventor as a single plant from the progeny of the aforementioned hybridization.

Asexual reproduction of 'Poulty040' by rooted cuttings was first done by Mogens N. Olesen in the nursery in Fredensborg, Denmark in July, 2018. This initial and other subsequent asexual propagations conducted in controlled environments have demonstrated that the characteristics of 'Poulty040' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulty040'. Specifically illustrated is a cluster of open flowers on a bare stemmed branch, a flower bud, open flowers viewed from above and the side, flower petals detached, sepals detached revealing reproductive flower parts, and leaves. Plants shown are 4 months old.

DETAILED DESCRIPTION OF THE VARIETY

The following is a description of 'Poulty040', as observed in its growth in an indoor glasshouse nursery in Odense Denmark. Observed plants are 4 months of age, and were grown on their own roots in 19 cm pots. Color references are made using The Royal Horticultural Society (London, England) Colour Chart, 2001, except where common terms of color are used.

For a comparison, several physical characteristics of the rose variety 'Poulpar029', U.S. Plant Pat. No. 16,148 are compared to the claimed plant. While 'Poulty040' has about 65 flower petals, 'Poulpar029' has 30 flower petals. The claimed plant has a flower diameter of 45 mm while 'Poulpar029' has a flower diameter of 35 mm. Open flowers of 'Poulty040' are generally Red Group 53B to 53C in color while 'Poulpar029' has a general tonality of Red Group 53A. The comparison variety produces flowers singly, while the new variety exhibits flowers in multiples of about 9 to 11 flower buds per flowering stem.

FLOWER AND FLOWER BUD

Blooming habit: Continuous.

Flower bud:

- *Size.*—Upon opening, 17 mm in length from base of receptacle to end of bud. Bud diameter is 10 mm.
- *Bud form.*—Globose.
- *Bud color.*—As sepals divide petals are Red Group 53A.
- *Sepal inner surface.*—Color: Yellow-Green Group 146D. Surface: Lightly pubescent.
- *Sepal outer surface.*—Color: Yellow-Green Group 144A. Texture: Smooth.
- *Sepal shape.*—Apex: Cirrhose. Base: Flat at union with receptacle.
- *Sepal margin.*—Margins have no foliaceous appendages.
- *Sepal size.*—About 22 mm long, 7 mm wide.
- *Receptacle.*—Texture: Smooth. Size: 6 mm in height, 5 mm wide. Color: Yellow-Green Group 144A. Shape: Funnel.
- *Pedicel.*—Surface: Smooth. Length: About 29 mm. Diameter: 2 mm on average. Color: Yellow-Green Group 144A. Strength: Strong.
- *Peduncle.*—Length: 2 to 3 cm. Diameter: About 2 mm. Color: Yellow-Green Group 144A. Texture: Small prickles.

Flower bud development: Flower buds are borne in clusters of about 9 to 11 flower buds per stem.

Flower bloom:

- *Fragrance.*—Light floral.
- *Duration.*—The blooms have a duration on the plant of approximately 19 days. Petals fall cleanly away from plant after flowers have fully matured.
- *Size.*—Flower diameter is 45 mm when open. Flower depth is 17 mm.
- *Flower shape.*—Star shaped rosette, very double, with many slightly overlapping petals of different sizes.
- *Shape of flower, side view.*—The upper portion is convex. The lower portion is flat.
- *Petalage.*—Under normal conditions about 65 petals.

General tonality of flower: Open flowers are Red Group 53B to 53C.

Petal color:

- *Upon opening, outer and inner petals.*—Upper surface: Red Group 53B. Lower surface: Red Group 54A with streaks of Red-Purple Group 69C.
- *Basal petal spots, upon opening.*—Upper surface: Moderate sized White Group N155B. Lower surface: Moderate sized White Group N155B.
- *After opening, outer and inner petals.*—Upper surface: Red Group 53B. Lower surface: Red Group 54A with streaks of Red-Purple Group 69C.
- *Basal petal spots, after opening, inner petals.*—Upper surface: Moderate sized White Group N155B. Lower surface: Moderate sized White Group N155B.

Petals:

- *Petal reflex.*—Strong bilateral reflexed.
- *Margin.*—Entire. Some petals have small point at apex. No undulations.
- *Shape.*—Broad and elliptic. Apex shape: Rounded. Base shape: Acute.
- *Size.*—26 mm (l)×20 to 25 mm (w).
- *Texture.*—Smooth.
- *Thickness.*—Average.

Petaloids:

- *Size.*—7 mm (l) by 6 mm (w).
- *Quantity.*—About 20.
- *Shape.*—Elliptical with an acute base and rounded apex.
- *Color.*—Red Group 53A on upper surface, Red Group 53B on lower surface. Streaks of White Group N155B.

Reproductive flower parts:

- *Pollen.*—None observed.
- *Anthers.*—Size: 2 mm in length. Color: Yellow Group 4D. Quantity: 25 on average.
- *Filaments.*—Color: Green-White Group 157A and Orange-Red Group N34C. Length: 4 mm.
- *Pistils.*—Length: 4 mm. Quantity: 20 on average.
- *Stigmas.*—Color: Yellow-Green Group 145D.
- *Styles.*—Color: Yellow-Green Group 145D.
- *Location of stigmas.*—Inferior in location relative to the length of the filaments and the height of the anthers.
- *Hips.*—None Observed.

PLANT

Plant growth: Upright and bushy. Plants are about 20 cm in height, and 36 cm wide.

Stems:

- *Color of juvenile growth.*—Yellow-Green Group 144B.
- *Color of mature growth.*—Yellow-Green Group 144A.
- *Length.*—Canes are about 12 cm from the base of the plant to the flowering portion.
- *Diameter.*—About 4 mm.
- *Internodes.*—On mature canes about 15 to 20 mm between nodes.
- *Surface texture.*—Young wood: Smooth. Older wood: Smooth.

Long prickles:

- *Incidence.*—10 prickles per 10 cm of stem.
- *Size.*—Average length of prickles on mature stems is 3 mm.

*Shape*.—Upper portion is linear. Lower portion is linear.

*Color*.—Juvenile prickles: Yellow-Green Group 145C. Mature prickles: Greyed-Red Group 180A.

Plant foliage:

*Compound leaf*.—85 mm (l)×48 (w).

*Quantity*.—4 leaves per 10 cm of stem on average.

*Leaf bearing angle to the stem*.—45 degrees.

*Color of juvenile foliage*.—Upper side: Yellow-Green Group 144A. Lower side: Yellow-Green Group 144B.

*Color of mature foliage*.—Upper side: Yellow-Green Group 147A. Lower side: Yellow-Green Group 146B.

Plant leaves and leaflets:

*Stipules*.—Size: 10 mm long, 3 mm wide. Quantity: 2 per compound leaf. Shape: Linear, slightly broad based with outward extending apex. Margins: Finely serrated. Color: Yellow-Green Group 144A.

*Petiole*.—Length: 11 mm. Diameter: 2 mm. Upper surface color: Yellow-Green Group 144A with intonations of Greyed-Purple Group 183C. Lower surface color: Yellow-Green Group 144A.

*Rachis*.—Length: About 34 mm. Upper surface color: Yellow-Green Group 144A with intonations of Greyed-Purple Group 183C. Lower surface color: Yellow-Green Group 144A.

*Leaflet*.—Quantity: Normally 5 to 7 leaflets. Margins: Serrated. Size: Terminal leaflets are about 31 mm long, 20 mm wide. Shape: Generally elliptical. Base: Rounded. Apex: Acuminate. Texture: Smooth. Thickness: Average. Arrangement: Odd pinnate. Venation: Reticulate. Glossiness: Slightly glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulty040' substantially as described and illustrated herein.

* * * * *

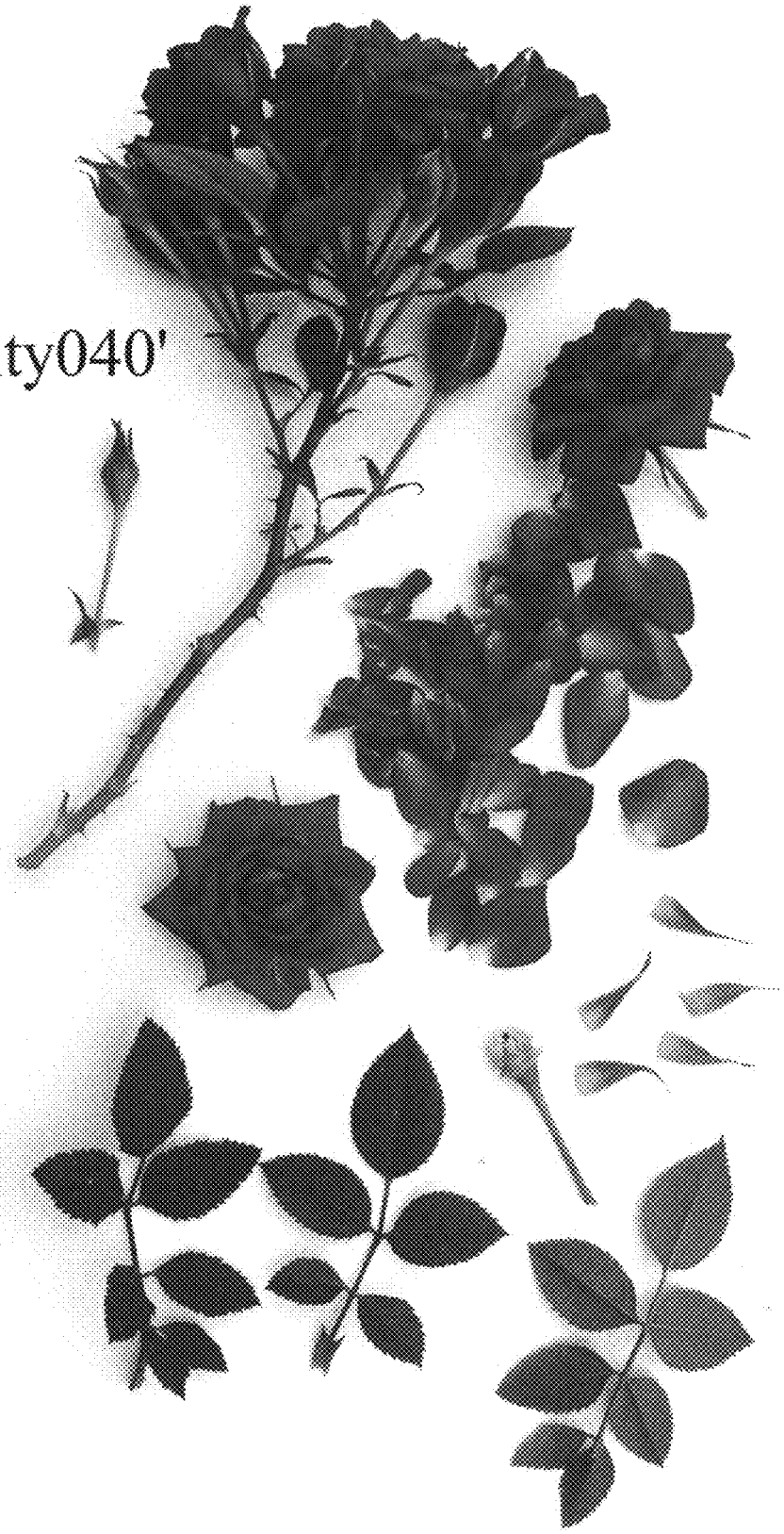
'Poulty040'